(12) United States Patent
Biedermann et al.

(10) Patent No.: US 10,905,482 B2
(45) Date of Patent: Feb. 2, 2021

(54) BONE ANCHORING ELEMENT (71) Applicant: BIEDERMANN TECHNOLOGIES GMBH & CO. KG, Donaueschingen (DE)

(72) Inventors: Lutz Biedermann, VS-Villingen (DE); Wilfried Matthis, Weisweil (DE); Helmar Rapp, Deisslingen (DE)

(73) Assignee: BIEDERMANN TECHNOLOGIES GMBH & CO. KG, Donaueschingen (DE)

(*) Notice: Subject to any disclaimer, the term of this patent is extended or adjusted under 35 U.S.C. 154(b) by 42 days.

(21) Appl. No.: 15/818,339

(22) Filed: Nov. 20, 2017

(65) Prior Publication Data
US 2018/0132916 A1 May 17, 2018

Related U.S. Application Data (63) Continuation of application No. 15/093,444, filed on Apr. 7, 2016, now Pat. No. 9,861,412, which is a
(Continued)

(30) Foreign Application Priority Data

Feb. 24, 2004 (DE) .................. 10 2004 009 429

(51) Int. Cl.
*A61B 17/86* (2006.01)
*A61B 17/68* (2006.01)
(Continued)

(52) U.S. Cl.
CPC .......... *A61B 17/8625* (2013.01); *A61B 17/68* (2013.01); *A61B 17/7001* (2013.01);
(Continued)

(58) Field of Classification Search
CPC .............. A61B 17/8625; A61B 17/744; A61B 2017/00867; A61B 17/7098;
(Continued)

(56) References Cited

U.S. PATENT DOCUMENTS 264,479 A 9/1882 Rogers
3,987,698 A 10/1976 Rabe
(Continued)

FOREIGN PATENT DOCUMENTS

CH 682450 A5 9/1993
DE 198 01 219 A1 7/1999
(Continued)

OTHER PUBLICATIONS

Office action for U.S. Appl. No. 14/469,264, dated Mar. 7, 2016, 7 pages.
(Continued)

*Primary Examiner* — Ellen C Hammond
*Assistant Examiner* — Tara Rose E Carter
(74) *Attorney, Agent, or Firm* — Lewis Roca Rothgerber Christie LLP (57) ABSTRACT

A bone anchoring element comprising a shaft (2) for anchoring in a bone, with a plurality of barb elements (7) arranged in at least one helical line around the shaft axis (M) is described, wherein said barb elements are elastically movable relative to the shaft. The bone anchoring element (1) is easy to press into a core hole bore in a bone. The barb elements (7) act in a similar manner as do the threads on a conventional bone screw and thus provide for depth positioning. Moreover, the barb elements at the same time secure the bone anchoring element and prevent it from sliding-out.

21 Claims, 11 Drawing Sheets

Related U.S. Application Data continuation of application No. 11/063,049, filed on Feb. 22, 2005, now Pat. No. 9,326,804.

(60) Provisional application No. 60/547,517, filed on Feb. 24, 2004.

(51) Int. Cl.
| | |
|---|---|
| *A61B 17/70* | (2006.01) |
| *A61B 17/72* | (2006.01) |
| *A61B 17/74* | (2006.01) |
| *A61B 17/00* | (2006.01) |

(52) U.S. Cl.
CPC ........ *A61B 17/701* (2013.01); *A61B 17/7007* (2013.01); *A61B 17/7032* (2013.01); *A61B 17/7266* (2013.01); *A61B 17/7291* (2013.01); *A61B 17/74* (2013.01); *A61B 17/864* (2013.01); *A61B 17/8685* (2013.01); *A61B 17/7037* (2013.01); *A61B 17/7098* (2013.01); *A61B 17/7283* (2013.01); *A61B 17/744* (2013.01); *A61B 17/746* (2013.01); *A61B 17/866* (2013.01); *A61B 2017/00867* (2013.01); *A61B 2017/8655* (2013.01)

(58) Field of Classification Search
CPC ..... A61B 17/866; A61B 17/846; A61B 17/86; A61B 17/863; A61B 17/864; A61B 17/8645
See application file for complete search history.

(56) References Cited

U.S. PATENT DOCUMENTS

| | | | |
|---|---|---|---|
| 4,259,076 A | 3/1981 | Yanney | |
| 4,331,423 A | 5/1982 | Yanney, Jr. | |
| 4,625,725 A | 12/1986 | Davison et al. | |
| 5,196,016 A | 3/1993 | Buser et al. | |
| 5,209,753 A | 5/1993 | Biedermann et al. | |
| 5,505,735 A | 4/1996 | Li | |
| 5,522,817 A | 6/1996 | Sander et al. | |
| 5,522,843 A * | 6/1996 | Zang | A61B 17/0401 606/232 |
| 5,562,704 A | 10/1996 | Tamminmäki et al. | |
| 5,577,912 A | 11/1996 | Prins | |
| 5,601,558 A | 2/1997 | Torrie et al. | |
| 5,645,589 A | 7/1997 | Li | |
| 5,662,654 A | 9/1997 | Thompson | |
| 5,727,943 A * | 3/1998 | Beaty | A61C 8/0022 433/174 |
| 5,735,898 A | 4/1998 | Brånemark | |
| 5,849,004 A | 12/1998 | Bramlet | |
| 5,947,965 A * | 9/1999 | Bryan | A61B 17/1757 606/250 |
| 5,984,927 A * | 11/1999 | Wenstrom, Jr. | A61B 17/0642 606/213 |
| 6,007,566 A | 12/1999 | Wenstrom, Jr. | |
| 6,083,227 A * | 7/2000 | Saurat | A61B 17/863 411/426 |
| 6,086,303 A | 7/2000 | Flückiger | |
| 6,283,691 B1 * | 9/2001 | Bogatz | F16B 33/004 411/371.1 |
| 6,428,317 B1 | 8/2002 | Abel | |
| 6,447,513 B1 | 9/2002 | Griggs | |
| 6,508,830 B2 * | 1/2003 | Steiner | A61B 17/0401 606/232 |
| 6,660,008 B1 | 12/2003 | Foerster et al. | |
| 6,843,791 B2 | 1/2005 | Serhan | |
| 7,879,036 B2 | 2/2011 | Biedermann et al. | |
| 8,080,044 B2 | 12/2011 | Biedermann et al. | |
| 8,292,932 B2 | 10/2012 | Matthis et al. | |
| 8,486,121 B2 | 7/2013 | Biedermann et al. | |
| 8,657,860 B2 | 2/2014 | Biedermann et al. | |
| 8,845,702 B2 | 9/2014 | Matthis et al. | |
| 2001/0007074 A1 * | 7/2001 | Strobel | A61B 17/8615 606/314 |
| 2001/0051807 A1 | 12/2001 | Grafton | |
| 2003/0045885 A1 | 3/2003 | Margulies et al. | |
| 2003/0088251 A1 * | 5/2003 | Braun | A61B 17/7022 606/263 |
| 2004/0068262 A1 | 4/2004 | Lemos et al. | |
| 2004/0122431 A1 | 6/2004 | Biedermann et al. | |
| 2004/0267264 A1 | 12/2004 | Konieczynski et al. | |
| 2005/0159749 A1 | 7/2005 | Levy et al. | |
| 2005/0165395 A1 | 7/2005 | Orbay et al. | |
| 2005/0187555 A1 | 8/2005 | Biedermann | |
| 2005/0203522 A1 | 9/2005 | Vaughan | |
| 2006/0264952 A1 | 11/2006 | Nelson et al. | |

FOREIGN PATENT DOCUMENTS

| | | |
|---|---|---|
| DE | 197 31 298 A1 | 11/1999 |
| DE | 299 14 192 U1 | 11/1999 |
| DE | 10 2004 009 429 A1 | 9/2005 |
| EP | 0 340 159 A1 | 3/1989 |
| EP | 0714643 A1 | 6/1996 |

OTHER PUBLICATIONS

Office action for U.S. Appl. No. 11/482,374, dated Oct. 1, 2008, 8 sheets.
Final Office action for U.S. Appl. No. 11/482,374, dated Jan. 22, 2010, 10 sheets.
Office action for U.S. Appl. No. 11/482,374, dated May 11, 2010, 13 sheets.
Final Office action for U.S. Appl. No. 11/482,374, dated Dec. 8, 2010, 11 sheets.
Office action for U.S. Appl. No. 13/617,923, dated May 2, 2013, 7 sheets.
Office action for U.S. Appl. No. 11/499,034, dated Nov. 18, 2008, 8 sheets.
Final Office action for U.S. Appl. No. 11/499,034, dated May 28, 2009, 12 sheets.
Office action for U.S. Appl. No. 11/499,034, dated Oct. 26, 2009, 9 sheets.
Final Office action for U.S. Appl. No. 11/499,034, dated Mar. 29, 2010, 13 sheets.
Office action for U.S. Appl. No. 12/908,826, dated Dec. 14, 2012, 7 sheets.
Office action for U.S. Appl. No. 11/646,973, dated Dec. 26, 2008, 9 sheets.
Final Office action for U.S. Appl. No. 11/646,973, dated Jun. 25, 2009, 10 sheets.
Final Office action for U.S. Appl. No. 11/646,973, dated Oct. 28, 2009, 8 sheets.
Final Office action for U.S. Appl. No. 11/646,973, dated Jan. 22, 2010, 9 sheets.
Office action for U.S. Appl. No. 11/646,973, dated May 11, 2010, 7 sheets.
Final Office action for U.S. Appl. No. 11/646,973, dated Oct. 13, 2010, 9 sheets.
Office action for U.S. Appl. No. 13/285,784, dated Jul. 30, 2012, 9 sheets.
European Search Report dated Apr. 13, 2005 for Application No. 05002783.8-1526.
Office action dated Feb. 24, 2015 for U.S. Appl. No. 14/469,264, 6 pages.
Office action dated Aug. 11, 2015 for U.S. Appl. No. 14/469,264, 8 pages.

* cited by examiner

BONE ANCHORING ELEMENT

CROSS-REFERENCE TO RELATED APPLICATION(S)

This application is a continuation of U.S. Pat. No. 15,093,444, filed Apr. 7, 2016, which is a continuation of U.S. patent application Ser. No. 11/063,049, filed Feb. 22, 2005, issued as U.S. Pat. No. 9,326,804, which claims the benefit of the filing date under 35 U.S.C. § 119(e) of Provisional U.S. Patent Application Ser. No. 60/547,517, filed Feb. 24, 2004, and which claims foreign priority benefits pursuant to 35 U.S.C. § 119(a)-(d) for German Patent Application 10 2004 009 429.2, filed Feb. 24, 2004, the disclosures of which are fully incorporated herein by reference.

BACKGROUND

The present invention relates to a bone anchoring element.

A known form of a bone anchoring element is a bone screw comprising a shaft with a thread for screwing the screw into a bone. The bone screw is manually inserted into the bone by means of a screw driver, which is a time-consuming and force-requiring process. Moreover, during the process in which the screw is inserted into the bone, high pressure forces may be acting on the bone itself, which is undesirable in some cases. For this reason, manually inserted bone screws are not used for certain clinical applications in neurosurgery, spinal surgery, pediatric surgery or trauma surgery.

It is therefore desirable to provide a bone anchoring element, which can be inserted into the bone more rapidly, more easily, and with less force than conventional bone screws. It is also desirable to provide a bone anchoring element that is versatile and useful in many clinical requirements. Preferably the bone anchoring element does not exert damaging forces on the bone, provides for secure attachment, and yet still can be inserted more deeply than conventional bone screws and/or removed in a screw-like fashion.

EP 0 714 643 A1 discloses a bone fixation device such as a screw, pin, staple, cable or anchor which has a micro-textured contact surface to enhance installation or gripping characteristics of the device. The micro-textured contact surface includes for example, angled rasp teeth, which bite or flex to resist movement in one direction and yet flex or slide to allow a relatively easy contact movement in the other direction. DE 198 01 219 A1 discloses a bone nail having rigid barb-like projections being arranged in circumferential rows around the nail.

BRIEF SUMMARY

The present invention is directed to a bone anchoring element that facilitates the rapid and secure anchoring to the bone by pressing the bone anchoring element into a prepared core hole in the bone. Barb elements are arranged on at least one helical line around the shaft axis of the bone anchoring element. The barb elements provide for a thread-like function, which allows the bone anchoring element to be positioned deeper into the bone by means of a screwing-in motion similar to that used with bone screws. Moreover, the barb elements prevent the bone anchoring element from being pulled out or coming loose. In addition, the bone anchoring element of the instant invention can be removed, if required, just like a screw, by turning it in the opposite or counterclockwise direction from which it was inserted.

In a modified version of the first embodiment of the bone anchoring element, the barb elements of the bone anchoring element are made of a body compatible alloy with shape memory and/or super-elastic properties.

In a second embodiment of the invention, a bone anchoring element with a thread is provided as well as method of forming the thread into the actual bone anchoring element.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

FIG. 13a) to 13c) shows a bone anchoring element according to a second embodiment at different stages of the manufacture of a bone anchoring element according to a second embodiment;

DETAILED DESCRIPTION OF THE DRAWINGS AND PRESENTLY PREFERRED EMBODIMENTS

The invention and various embodiments thereof are presented in FIGS. 1 to 23 and the accompanying descriptions wherein like numbered items are identical.

A bone anchoring element according to a first embodiment of the invention is described with reference to FIGS. 1 to 7. The bone anchoring element, 1, comprises a shaft, 2, with a tip, 3, at one end, and a head, 4, at the other end. The shaft, 2, is cylindrical in shape and comprises a plurality of grooves, 5, 5' which extend parallel to a shaft axis M. The plurality of grooves, 5, 5', are open at their end facing the tip 3, and are closed, preferably in a rounded fashion, at their end facing head 4. Although the grooves, 5, 5', shown in FIG. 3 have a dovetail-shaped profile, the profile can also be of any other shape, such as for example a T shape. In addition, the closed end of the groove can be any other shape desired. In the example shown in FIG. 3, three grooves 5 are provided at equal distances along the direction of the circumference of shaft 2. However, any number of grooves desired can be used provided that the grooves fit around the circumference of the shaft. Therefore, at least two, three or more than three grooves can be provided along the circumference of the shaft 2.

Figures 1, 2, 3:
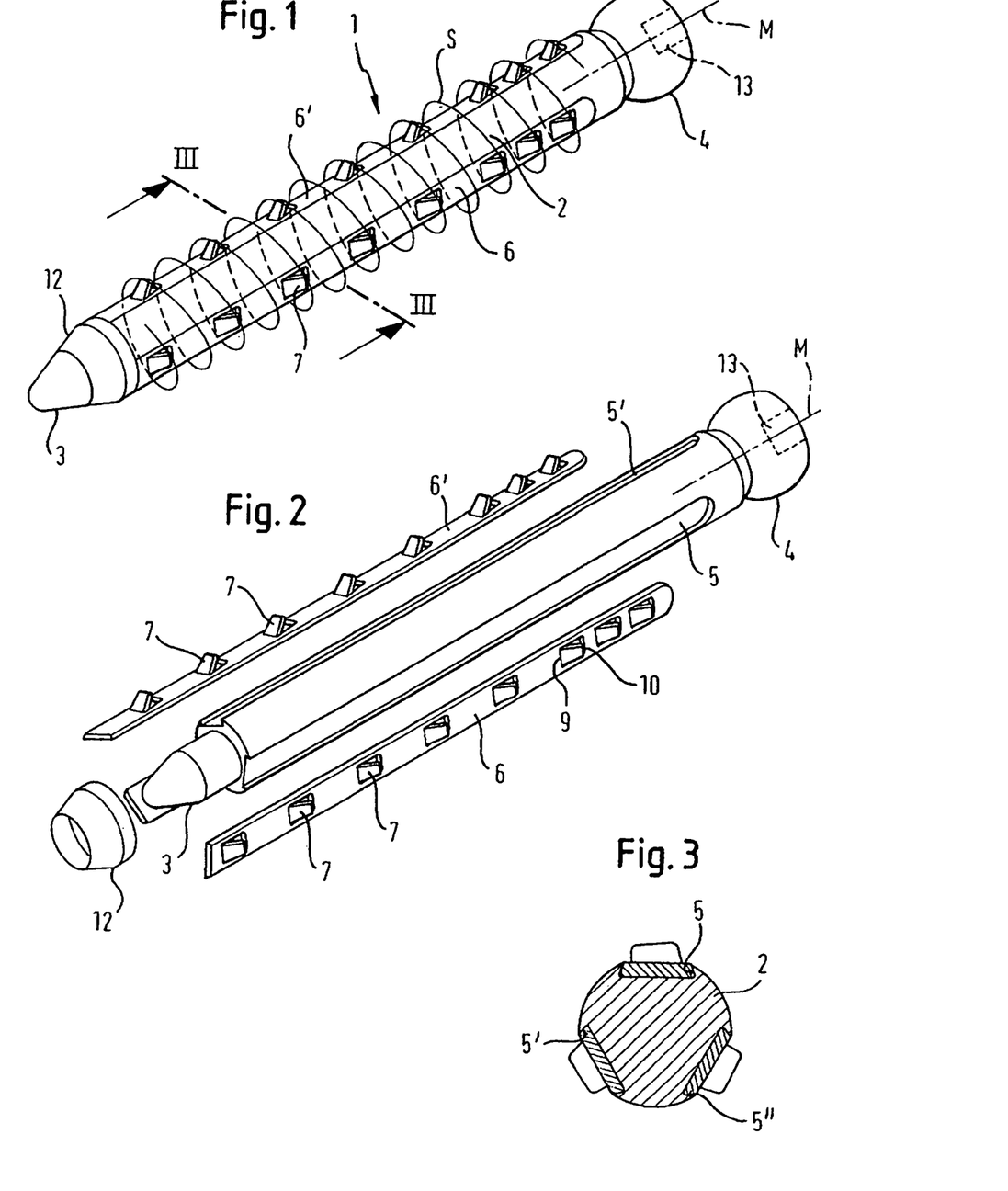
FIG. 1 shows a perspective view of a bone anchoring element according to a first embodiment.
FIG. 2 shows a perspective exploded view of the bone anchoring element according to FIG. 1.
FIG. 3 shows a sectional view of the bone anchoring element according to FIG. 1, along the line, III-III.

Plates 6, 6' with a cross-section matching that of grooves 5 are inserted into grooves 5 in a sliding fashion and are held therein in a fitting or mating fashion. Preferably the plates are oblong in shape and made of a body-compatible metal. However, the plates can be made of other types of body-compatible materials in other shapes provided that the plates abut the shaft and rest in the grooves 5 in a fitting or mating fashion.

Figures 4, 5, 6:
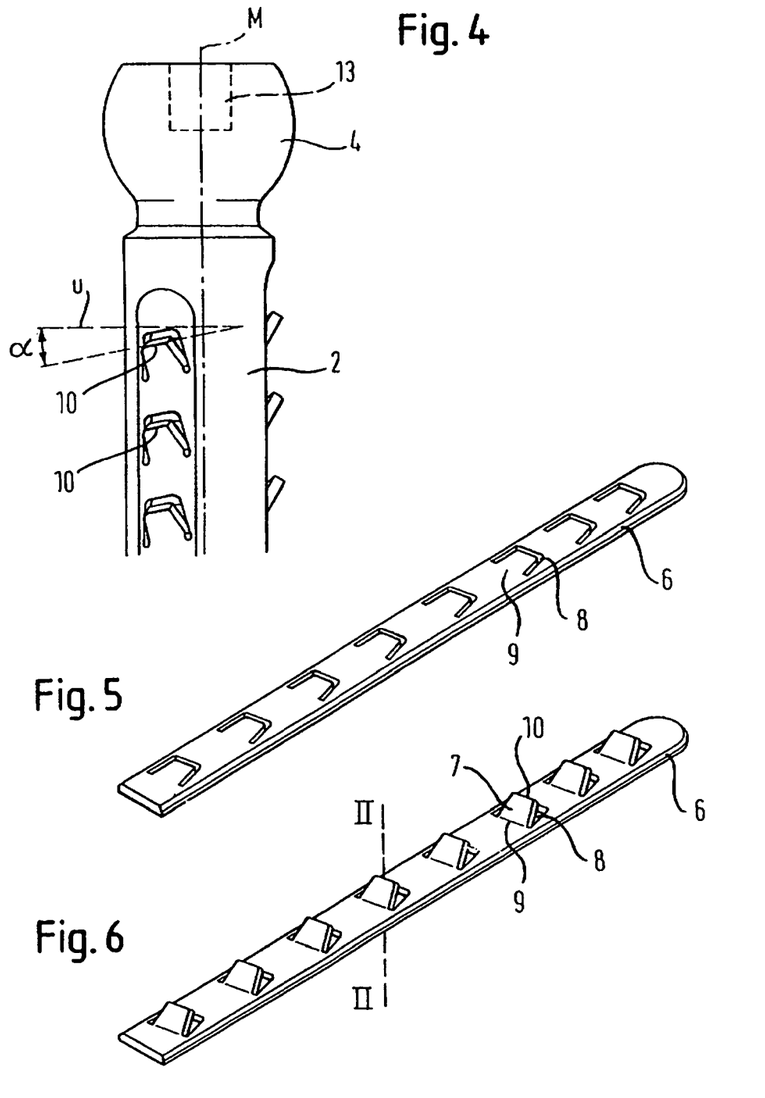
FIG. 4 shows an magnified perspective exploded view of a detail of the bone anchoring element according to FIG. 1.
FIG. 5 shows a perspective view of an element of the bone anchoring element having a plate with barb elements according to FIGS. 1 to 4 in a collapsed state.
FIG. 6 shows a perspective view of the bone anchoring element having a plate with barb elements according to FIG. 5 in an expanded state.
Figure 7:
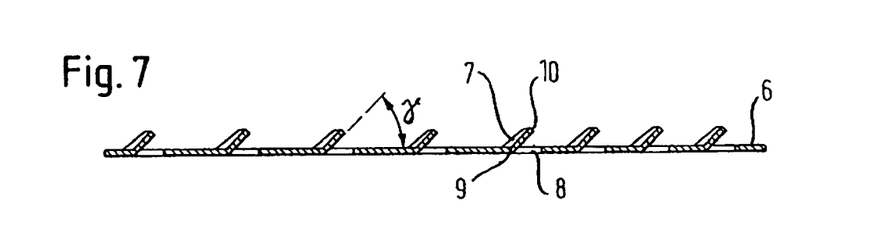
FIG. 7 shows a sectional view of the bone anchoring element according to FIG. 6, along the line, II-II, in FIG. 6.

The plates, 6, each include a plurality of barb elements 7. As is best seen in FIGS. 5 to 7, barb elements 7 are formed by essentially trapezoidal shaped cuts 8 being made in the plates 6. The end base 9 of the trapezoidal shaped cuts 8 is not cut-out from the plate and acts as the attachment and the bending site for barb elements 7 in the plate 6, 6'. Barb elements 7 are preferably arranged such that when the plates are inserted into grooves 5, the wider end base, 9, of the barb element faces the tip 3 while the narrower free ends, or the cutting edges, 10, of barb elements 7 face the head 4.

As can be seen from FIGS. 5 to 7, barb elements 7 project from the surface by a predetermined angle γ which is selected during the manufacturing process based upon the material used and the actual dimensions of barb elements 7 so that a desired stiffness of the barb element is obtained. Due to their configuration and attachment, onto the plate, barb elements 7 are elastically deformable relative to the body of the shaft. When the barb elements 7 are collapsed or pressed into cuts 8, they are pre-tensioned.

As is evident from FIG. 1, barb elements 7 of one plate 6 are arranged relative to barb elements 7 of a neighboring plate 6' in axial direction on at least one helical line S around shaft axis M. While a single continuous helical line S is illustrated, plural parallel helical lines can also be used. Furthermore, the distances between the barb elements can be varied along the length of the shaft of the bone anchoring element as desired.

Moreover, as is further seen in the magnified representation according to FIG. 4, the essentially trapezoidal-shaped cuts, 8, are inclined with regard to the circular circumference line, U, by an angle, α, which corresponds to the helical angle of helical line S. The free ends, 10, of the barb elements are thus positioned on helical line S such that they form cutting edges similar to the crest of a screw thread.

As is further evident from FIGS. 1 and 2, the embodiment shown is provided with an area close to the head in each turn of imaginary helical line S with a barb element, 7, and with an area adjacent to tip 3 in every other turn with a barb element.

Furthermore, as seen in FIG. 2, tip 3 also has a smaller diameter than shaft 2 in a section that is adjacent to the end of the shaft 2 in order to facilitate the insertion of plates 6 into the grooves 5. In the assembled state, wherein the plates 6, have been inserted into grooves 5 by sliding the plates into the grooves, a ring-shaped securing element 12 is also provided to prevent the plates from sliding out of the groove. The ring-shaped securing element 12 has a first end and a second end which tapers in a cone-shaped section in the direction of tip 3 and connects flush to the tip. The first end of the ring shaped securing element abuts with the shaft 2 as well as plates to prevent the plates 6 from sliding out of the grooves. Securing element 12 is firmly attached to the tip. Preferably the securing element is welded onto the shaft. Other means of attachment are possible.

In the first embodiment, the head 4 of the bone anchoring element is a spherically shaped segment. The head 4 has a recess 13, on its side facing away from the tip of the shaft. The recess 13 can be used during insertion of the bone anchoring element for engagement of a screwing-in tool, such as a screw driver.

The bone anchoring element can be made of any body-compatible material. Preferably a body-compatible metal, such as for instance titanium, or a body-compatible plastic material can be used. Examples of other body-compatible materials include stainless steel, titanium alloys, nickel-titanium alloys, nitinol, chrome alloy, cobalt chrome alloys, shape memory alloys, materials with super elastic properties, carbon reinforced composites, silicone, polyurethane, polyester, polyether, polyalkene, polyethylene, polyamide, poly(vinyl) fluoride, polyetheretherketone (PEEK), polytetrafluoroethylene (PTFE). In addition, the bone anchoring element can be made of shape memory materials or alloys, such as nickel titanium or nitinol. Furthermore, the bone anchoring element can possibly be made from a bioabsorbable material. Examples of bioabsorbable materials include polylactides, and polyanhydrides. Plates 6 are made of the same material as the shaft or of a different material if a different material is desired to ensure that the barb elements 7 on the plates have the necessary elastic properties. The securing element can be of any biocompatible material.

The entire bone anchoring element or only the shaft and/or the plates can be coated with a bioactive material such as for example growth factors for bone ingrowth and bony attachment, or for soft tissue ingrowth. Non-limiting examples of growth factors include insulin-like growth factor 1, basic fibroblast growth factor, transforming growth factor, platelet-derived growth factor, bone-derived growth factors, arginine, bone morphogenetic protein, LIM mineralization protein, and combinations thereof. The bioactive material can facilitates in healing.

Furthermore, the entire bone anchoring element or only the shaft and/or plates can be roughened to provide a texture on their surfaces. The texture can be a microtexture in the form of bumps, pyramids, rods, and so forth. The texture can be applied by processes known in art. The roughened texture provides improved anchoring of the screw to the bone.

Figure 8A:
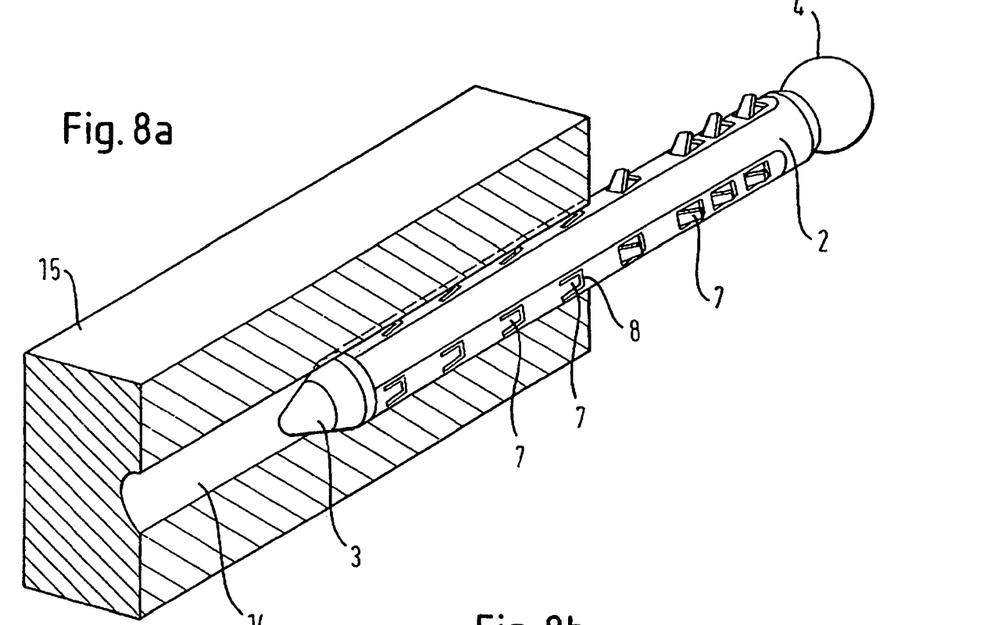
FIG. 8a) shows a schematic view of a first step of the insertion of the bone anchoring element according to FIGS. 1 to 7.

In operation, the anchoring element, 1, is initially preassembled by inserting the pre-made plates 6, 6', which are already provided with barb elements 7, into grooves 5, 5' followed by firmly connecting the securing element, 12, to the tip of the shaft. In use, as is shown schematically in FIGS. 8a) and 8b), a core hole, 14, is prepared first in the bone, 15. The diameter of the core hole corresponds essentially to the diameter of shaft 2 or it can be slightly larger or smaller, depending upon the desired result or circumstances. The diameter of the core hole 14 is selected depending on the diameter of the shaft 2 and the flexibility of the barb elements so that the desired resistance is provided by the barb elements. The selected diameter depends also upon the bone quality, for example it can be selected larger for healthy hard bone and smaller for osteoporotic weak bone Subsequently, as shown in FIG. 8a), the bone anchoring element, 1, is inserted into core hole 14. As the bone anchoring element is being inserted into the core hole 14 of bone 15, the barb elements 7 are in a collapsed state and are pressed against or into the cuts, 8, due to their elasticity. The sliding motion enables the bone anchoring element to be inserted very rapidly, in contrast to the conventional bone screws using the screwing-in process. When inserted, the pre-tensioned barb elements, 7, expand and rise up and press with their cutting edge, 10, outwardly against the wall of core hole 14, as is evident from FIG. 8b). The barb elements prevent the bone anchoring element from being pulled out or from falling out of the core hole 14.

Figure 8B:
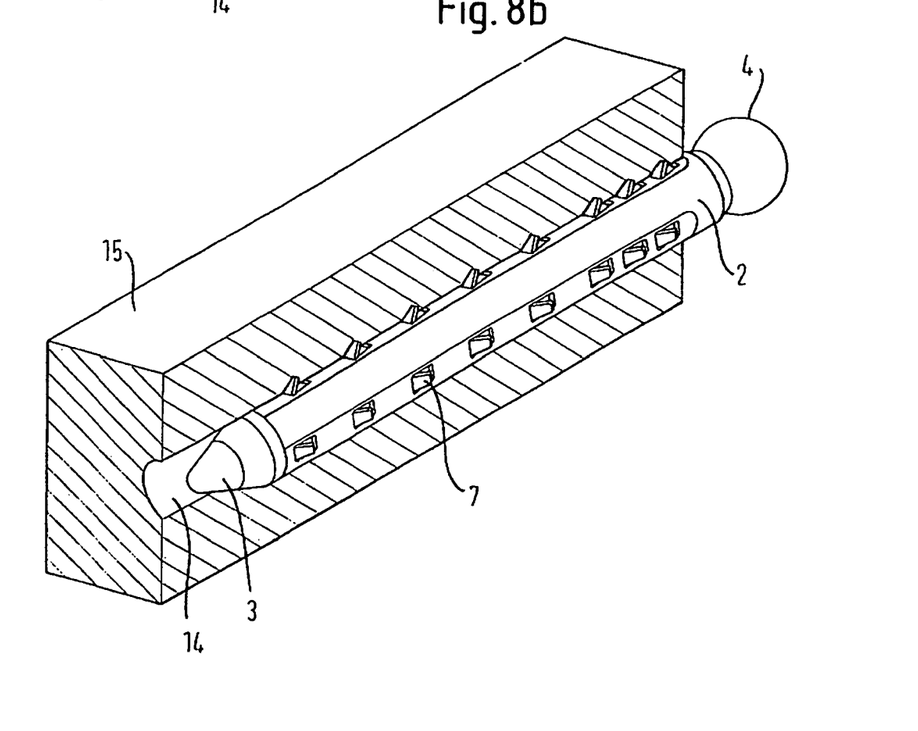
FIG. 8b) shows a schematic view of a bone anchoring element according to FIGS. 1 to 7 in the inserted state.

For further and/or final positioning of the bone anchoring element in the core hole 14, or for positioning of the head, 4, the bone anchoring element is screwed further into core hole 14 or screwed out there from, like a screw, by means of a turning motion with a screwing-in tool engaging the recess 13 in the head 4. During the process, the cutting edges, 10, of the barb elements, being positioned on helical line S, act like the crest of a thread. The bone anchoring element can be removed just like a bone screw by turning it in a counter-clockwise direction.

In most cases, a conventional bone screw requires not only that the core hole is drilled into the bone, but in also that the bone threads are cut into the bone. In all cases with the insertion of a conventional bone screw, a repeated turning motion is required. Compared to the time required to anchor a conventional bone screw, the time required to insert the bone anchoring element according to the instant invention is substantially shorter due to the fact that the bone anchoring element slides or glides into the core hole 14 without having to encounter the forces of the screw thread on the core hole 14 and bone 15. Nonetheless, because of its design and configuration, the bone anchoring element does not fall out of the core hole 14.

Figures 9A, 9B:
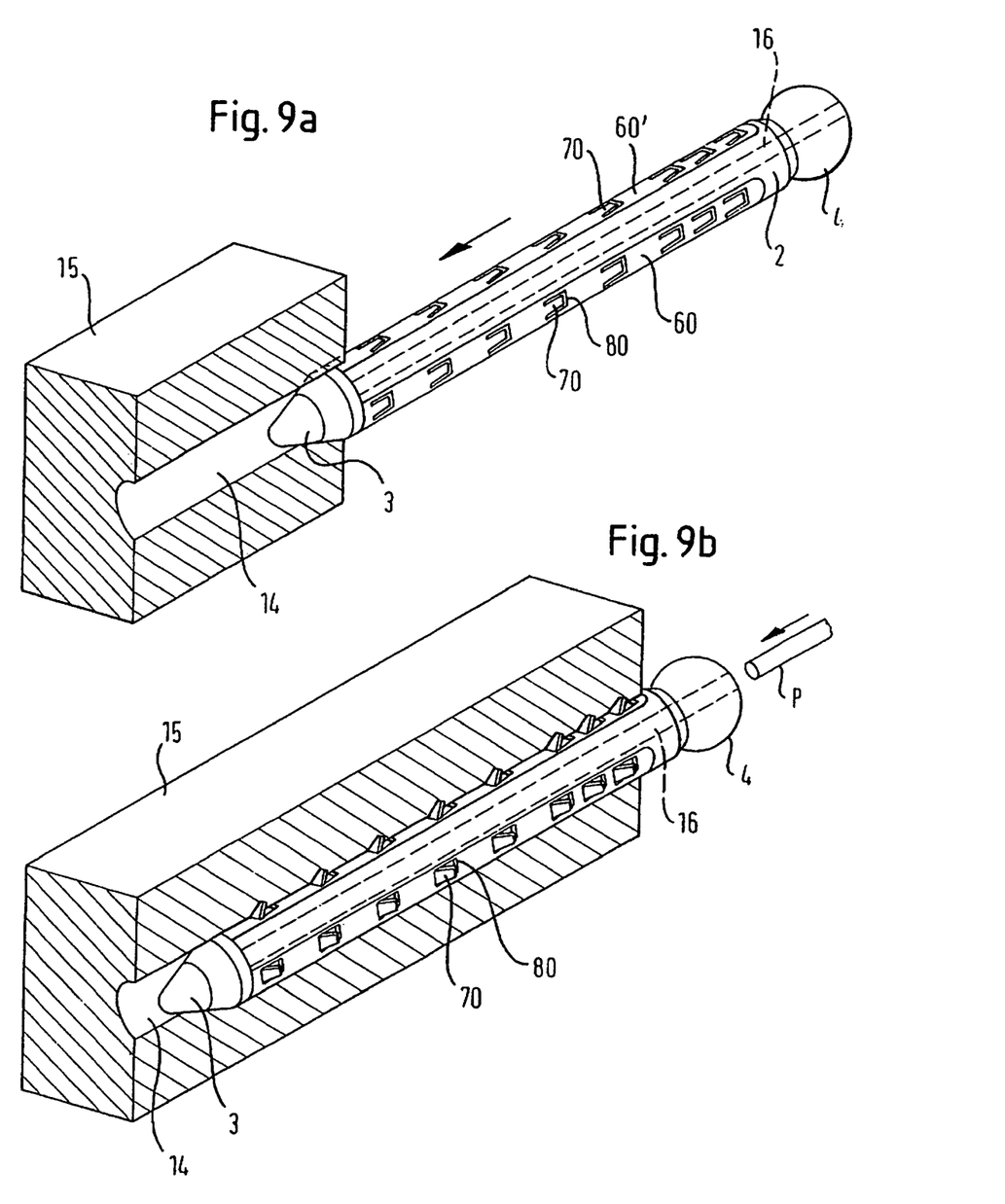
FIG. 9a) shows a schematic view of a first step of the insertion of a modified bone anchoring element according to FIGS. 1 to 7.
FIG. 9b) shows a schematic view of a second step of the insertion of the modified bone anchoring element.

A modification of the first embodiment and its operation are shown in FIGS. 9a) and 9b). This embodiment differs from the first embodiment in that at least plates 60 with barbs 70 consist of a body-compatible alloy with shape memory and/or super-elastic properties. An example of such an alloy is a titanium-nickel alloy, preferably nitinol. For this embodiment, the plates 60 are fabricated so that at a predetermined higher temperature, the barb elements 70 expand and project outwards from the shaft, whereas at a temperature that is lower relative to this predetermined higher temperature, the barb elements 70 are collapsed and reside within cuts 80. As seen in FIG. 9a), the bone anchoring element slides into core hole 14, with the barb elements 70 collapsed and residing within the cuts 80. Once the bone anchoring element slides in the core hole, as is shown in FIG. 9b), a heating device such as a heating cartridge P can be inserted into a coaxial bore hole, 16, inside the bone anchoring element. The heating cartridge P can heat the bone anchoring element to the predetermined temperature, whereby the ensuing phase transition of the crystal structure of the metal plates causes barb elements 70 to deploy and rise up and press against the wall of core hole 14. The heating cartridge can then be removed from the coaxial bore hole 16.

This modified embodiment provides the advantage that it reduces the amount of force that is required to press the bone anchoring element into core hole 14 and enables the adjustment of the bone anchoring element to a desired depth by the sliding motion during its insertion as long as barb elements 70 are in a collapsed state and do not press against the wall of core hole 14. Due to the presence of super-elastic alloy, barb elements 70 can show approximately 8 percent to 10 percent of stretching compared to approximately one percent stretching with conventional metals. The higher elasticity of the barb elements in this embodiment simplifies the handling and provides additional security in anchoring the bone anchoring element in the bone.

Figures 10, 11A:
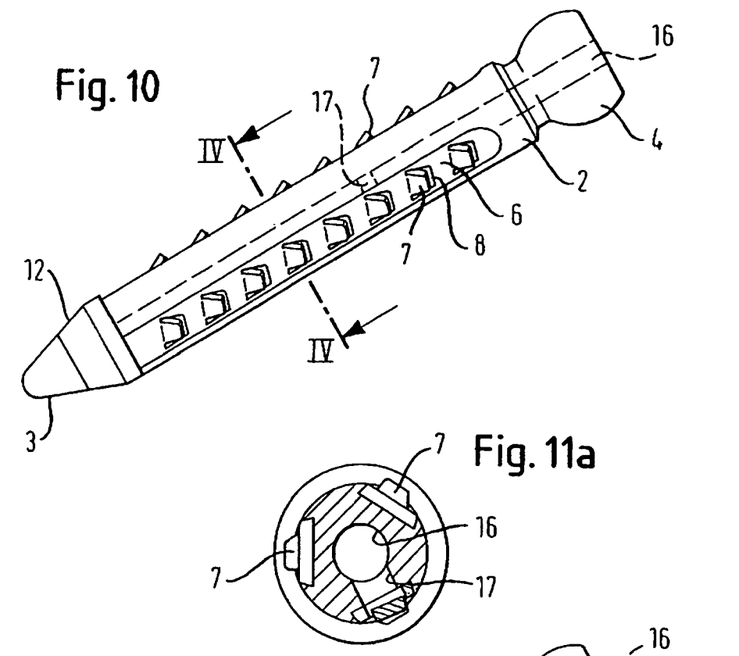
FIG. 10 shows a schematic view of a bone anchoring element according to another modification of the first embodiment.
FIG. 11a) shows a sectional view of the bone anchoring element according to FIG. 10, along the line, IV-IV.
Figure 11B:
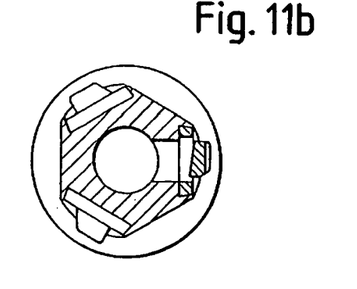
FIG. 11b) shows another different cross-sectional view of the bone anchoring element described in FIG. 10, along the line, IV-IV.
Figure 11C:
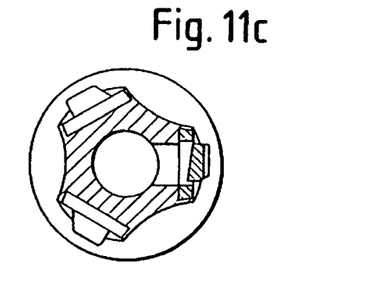
FIG. 11c) shows yet another different cross-sectional view of the bone anchoring element described in FIG. 10, along the line, IV-IV.

Yet another modification of the first embodiment is shown in FIGS. 10 and 11. In this embodiment, the anchoring bone element comprises a coaxial bore hole, 16, as described with respect to the previous embodiments, which extends from the free end of head 4 to the end of shaft 2 in the center of the shaft. Coaxial bore hole 16 is connected to cuts 8 in the plates 6 by means of radial bore holes 17 which extend in a radial direction from the coaxial bore hole 16 to the outer circumference of the shaft.

FIG. 11 a) shows a cross-sectional view of the bone anchoring element 1 of FIG. 10 along the line IV-IV having a first shaft configuration. The shaft 2, as seen in FIGS. 11 b) and 11 c) can also be made of different configurations. For example, the shaft 2 can be made in a shape so as to provide the slat-like cross section as seen in FIG. 11 b) or concave cross-section as seen in FIG. 11 c).

In operation, following the insertion and positioning of the bone anchoring element at its desired insertion depth, coaxial bore hole 16 and radial bore holes 17, can be used to deliver to the surrounding bone area either bone cement or any active ingredient, such as a drug or growth-promoting substance. The bone cement can be used for additional anchoring, with the cement exiting through cuts 8 and hardening thereafter. The number of the radial bore holes, 17, need not correspond to the number of cuts 8, and therefore, there may be less radial bore holes 17 than cuts 8. In addition, the central bore hole, 16, may extend through the tip 3 so that the cement or active ingredient in the central bore hole 16 can also exit from tip 3.

Figure 12:
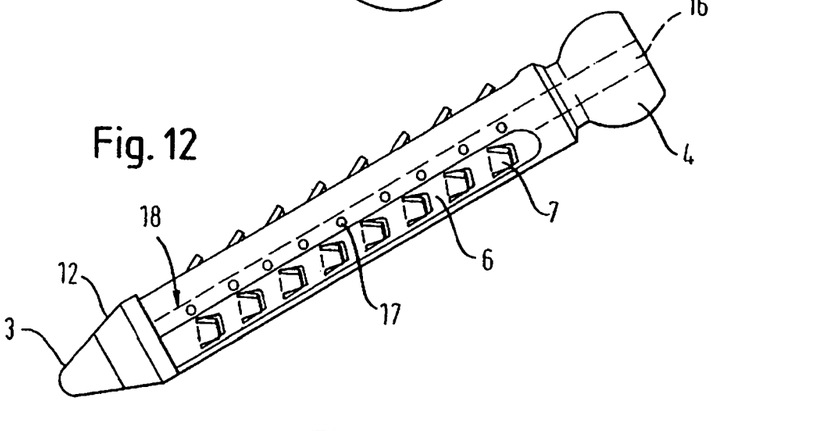
FIG. 12 shows a perspective view of a bone anchoring element according to another modification of the first embodiment.

In yet another modification shown in FIG. 12, the radial bore holes, 17, extending from the coaxial bore hole 16, do not face trapezoidal shaped cuts 8 of plates 6 in the direction of the circumference, but end in the wall sections, 18, of the coaxial bore hole 16, in which no plates 6 are provided.

Figures 13A, 13B, 13C:
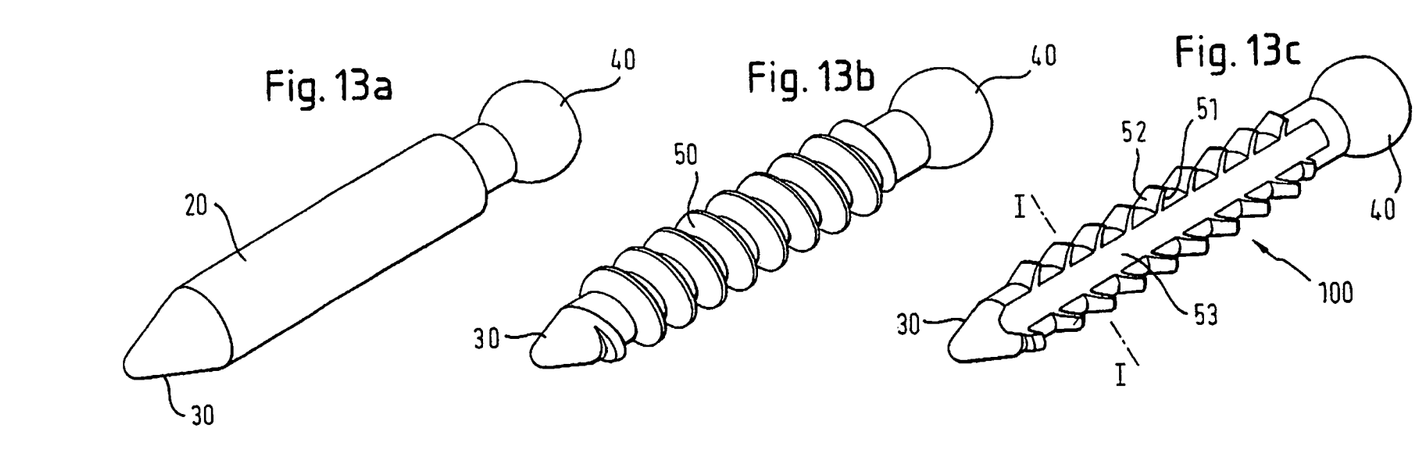
Figure 14:
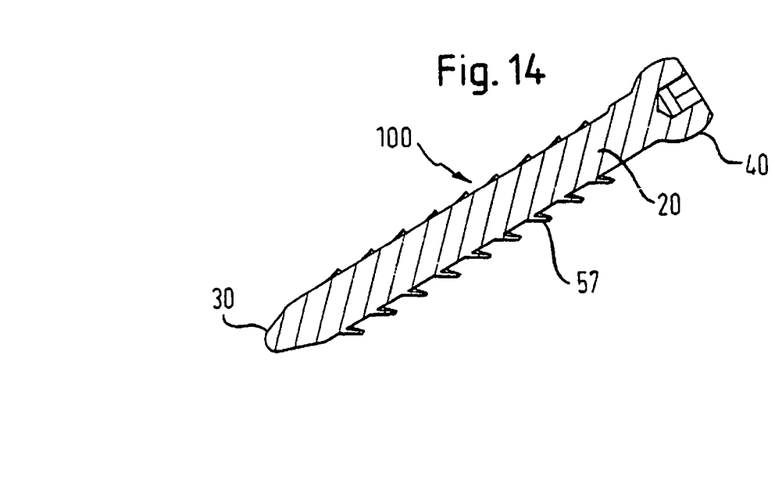
FIG. 14 shows a view of a longitudinal cross-sectional view of the second embodiment after the final manufacturing step shown in FIG. 13c)
Figure 15:
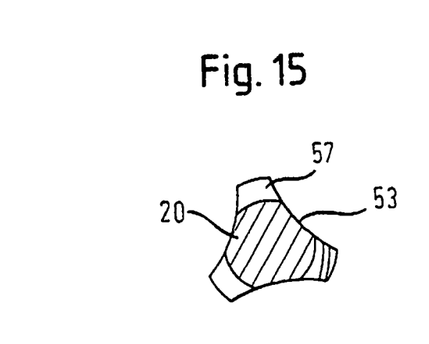
FIG. 15 shows a cross-sectional view through the shaft of the bone anchoring element according to FIG. 13c) of the second embodiment.

FIGS. 13a) to 13c) show a second embodiment of the instant invention at various stages of its manufacture and the steps of the manufacturing process. FIG. 14 shows a cross-section in the longitudinal direction of the bone anchoring element shown in FIG. 13c) after the final manufacturing step. FIG. 15 shows a cross-sectional view of the shaft of the bone anchoring element along line I-I according to the second embodiment shown in FIG. 13c.

As is seen from FIG. 13a), the first step of the manufacturing process of the second embodiment of the bone anchoring element 100 provides an bone anchoring element with a shaft, 20, a tip, 30, on one end of the shaft, and a head, 40, at the opposite end. In the second step of the manufacturing process shown in FIG. 13b), a thread, 50, is cut into shaft 20. In the next step, an undercut is generated in the thread 50 so that a partial flank, 51, facing head 40 and the partial flank, 52, facing tip 30 include an angle of only several degrees, as is seen in FIG. 13c). Preferably, the angle is between approximately 30° to 60°. The threads of this embodiment generate a certain degree of elasticity and act as barb elements. FIG. 13c), shows that sections 53 in the longitudinal direction of the shaft 20 are subsequently milled. Preferably the sections 53 are concave in shape towards the middle axis of the shaft and extend along the entire length of the shaft. At least two, but preferably more, sections 53 with equal mutual distances in the direction of the circumference are thus provided. In conjunction with the remaining thread parts with undercuts, this configuration generates barb elements 57 that are similar to barb elements 7 of the first embodiment.

The bone anchoring element according to this second embodiment is preferably made from a body-compatible plastic material, such as for example but not limited to a high-molecular polyethylene. Using a body-compatible plastic material for this embodiment is the easiest way to impart the necessary elasticity required of barb elements 57.

Additional modifications of the described embodiments are possible and elements of the individual embodiments and modifications thereof may be combined with each other.

For example, in another modification, the anchoring element, 100, according to the second embodiment can also have a coaxial bore hole and bore holes extending radially there from in the wall for the insertion of an active substances.

Furthermore, with any of these various embodiments or modifications, the barb elements need not be trapezoidal in shape. Rather the barb elements can be of any shape which imparts the desired characteristics to the barb element, including its elasticity, such as for example but not limited a square, or rectangular.

Unlike in the embodiment shown in FIG. 1, the barb elements of an axial row may be provided at equal distances in axial direction such that a barb element is present at that site of each helix. Alternatively, the distances between the barb elements of a row may vary in axial direction, whereby the distance in each case corresponds to a an integral multiple of a smallest distance between two barb elements of an axial row. Varying distances can be used to account for differences in bone density and to reduce the load on certain bone structures.

In yet another modification of the invention, the barb elements are made from a shape memory alloy such that they project at body temperature and are in a collapsed position at a lower temperature, e.g. at room temperature. In operation of the bone anchoring element made from a shape memory alloy, the bone anchoring element with collapsed barb elements is pressed into the core bore hole. After the bone anchoring element warms up and equilibrates to body temperature, the barb elements expand to their final position.

It is also possible to use a metal with correspondingly high elasticity as the material for the bone anchoring element according to the first embodiment or the plates with the barb elements or even the single-piece screw according to the second embodiment.

Moreover, an absorbable material can be used for the bone anchoring element. Plastic materials that are absorbable in the body like polylactide (PLLA).

In another modification, the tip, 3, may be provided as a separate piece which is connected to the shaft. For example, the tip 3 can be screwed to shaft 2. In this embodiment, the end of the shaft 2 facing the tip has a bore hole with internal thread whereas the tip has a section with external thread that can be screwed into the internal thread of the bore hole of the shaft. The tip can be connected to the shaft with other known connectors.

Figure 16:
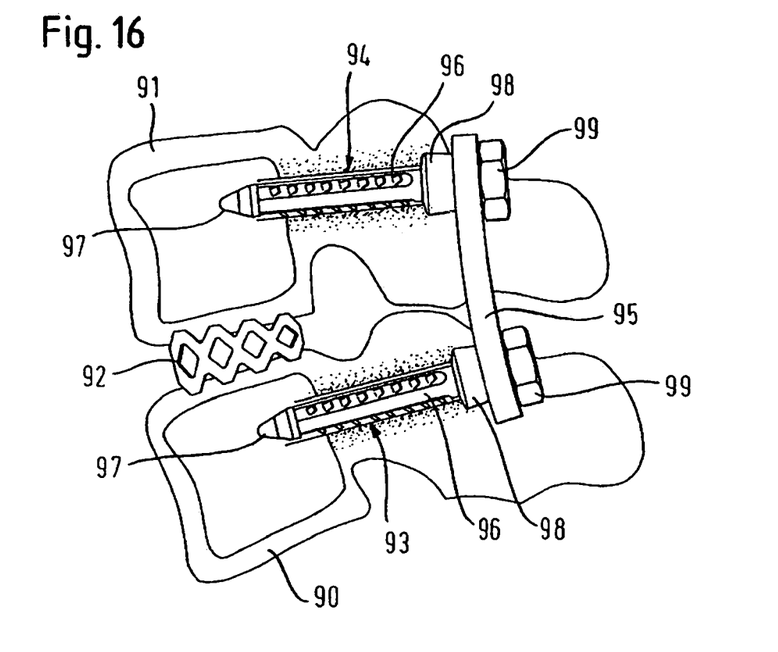
FIG. 16 shows an example of the application of the bone anchoring element in the form of a monoaxial screw.

FIG. 16 shows a first application example, in which two vertebrae 90, 91 are made more stiff and rigid, through the use of a fusion element, 92. Monoaxial bone anchoring elements 93, 94 are provided by means of which a rod, 95, is anchored in the vertebra. The monoaxial bone anchoring elements, 93, 94 each comprise a shaft, 96, with a tip, 97, with the shaft being provided according to one of the embodiments of the bone anchoring element described above. At the end of shaft 96 that is opposite to tip 97, a receiver member, 98, is provided which is rigidly connected to the shaft and in which rod 95 is inserted in known fashion and secured by means of a fixation element, 99, for instance by means of a nut screwed onto the receiver member. In the case of the monoaxial bone anchoring element, it is advantageous to provide shaft 96 with the plates having barb elements made from the shape memory alloy, since the bone anchoring element, after it is pressed into the core hole bore and before it is heated, is capable of pivoting inside the core hole bore allowing the alignment of receiver member 98 relative to the rod.

Figure 17:
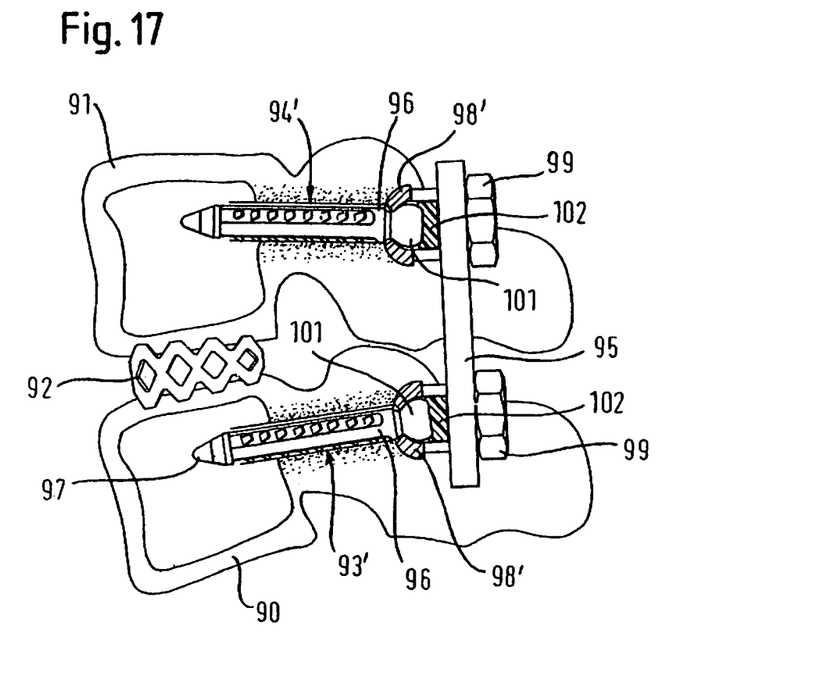
FIG. 17 shows an example of the application of the bone anchoring element in the form of a polyaxial screw.

FIG. 17 shows yet another application example of this invention. This example, differs from the application example according to FIG. 16 in that polyaxial bone anchoring elements are provided in place of the monoaxial bone anchoring elements. The polyaxial bone anchoring elements, 93', 94', comprise a shaft, 96, with a tip, 97, whereby shaft 96 is provided according to one of the embodiments of the anchoring element with barb elements according to the instant invention. At the end of shaft 96 that is opposite from tip 97, a head, 101, is provided which, in the non-fixed state, is held in a pivoting fashion in receiver member 98'. A rod, 95, can be placed in the receiver member in known fashion, with rod 95 pressing either directly (not shown) or by means of pressure member 102 (shown) onto head 101 thus effectively fixing the pivoting position of the head relative to the receiver member.

Figure 18:
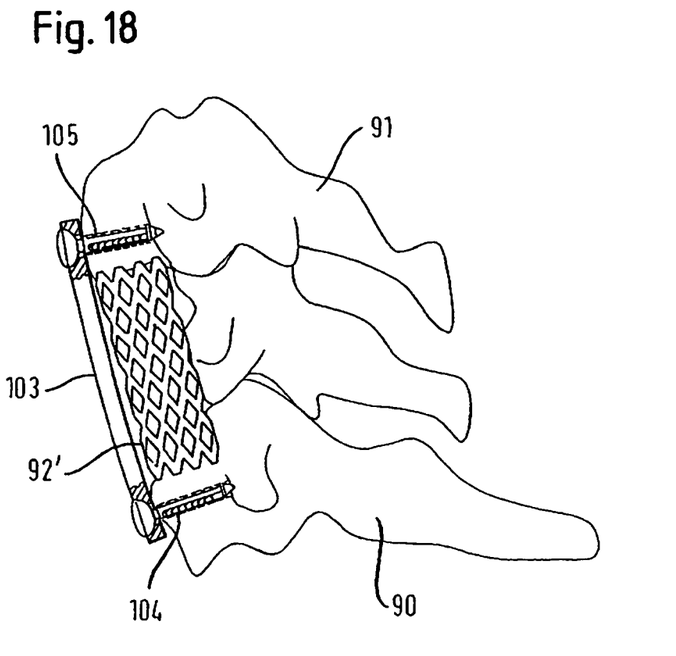
FIG. 18 shows an example of the application of the bone anchoring element in conjunction with a fusion element and a plate anchored in the vertebrae.

FIG. 18 shows as another application example, in which two vertebral bones 90, 91 are stabilized and made more rigid after removal of a portion between the vertebrae through the use of a fusion element, 92', and a plate, 103, which is anchored in the vertebrae by means of bone anchoring elements, 104, 105. The bone anchoring elements 104, 105 comprise a shaft with barb elements according to the invention and a head which is used to press plate 103 against the vertebral bone. The bone anchoring element can also be used in conjunction with plates that are in use in trauma surgery as shown by this example.

Figure 19:
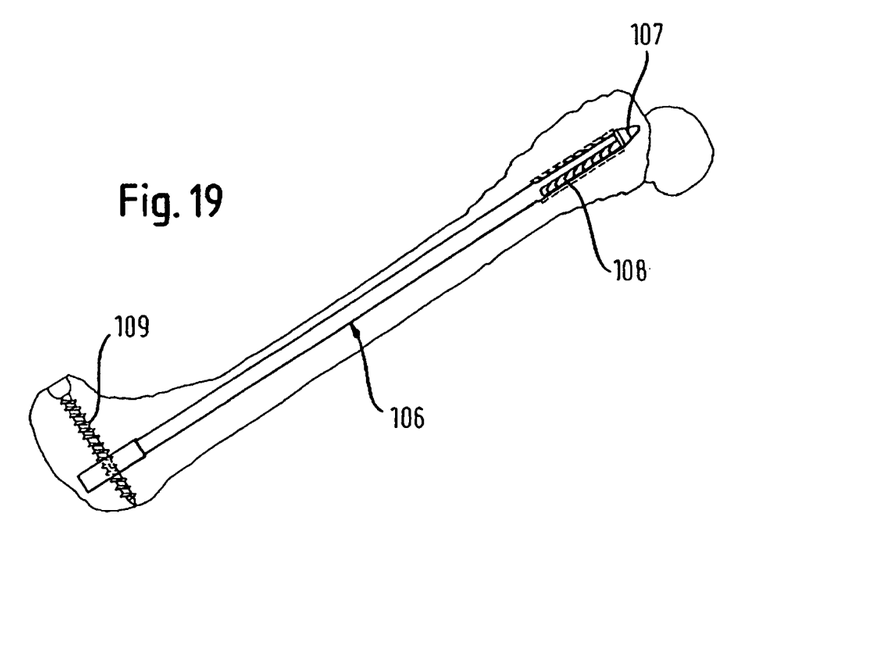
FIG. 19 shows an example of the application of the bone anchoring element in the form of a intramedullary nail.

FIG. 19 shows as another application example of the instant invention. In this example, an intramedullary nail, 106, comprises a shaft and a tip, 107. Adjacent to the tip, the shaft of the nail comprises a section, 108, which has barb elements like the bone anchoring element according to the invention. The intramedullary nail is inserted into a tubular bone and secured by means of a screw, 109.

Figure 20:
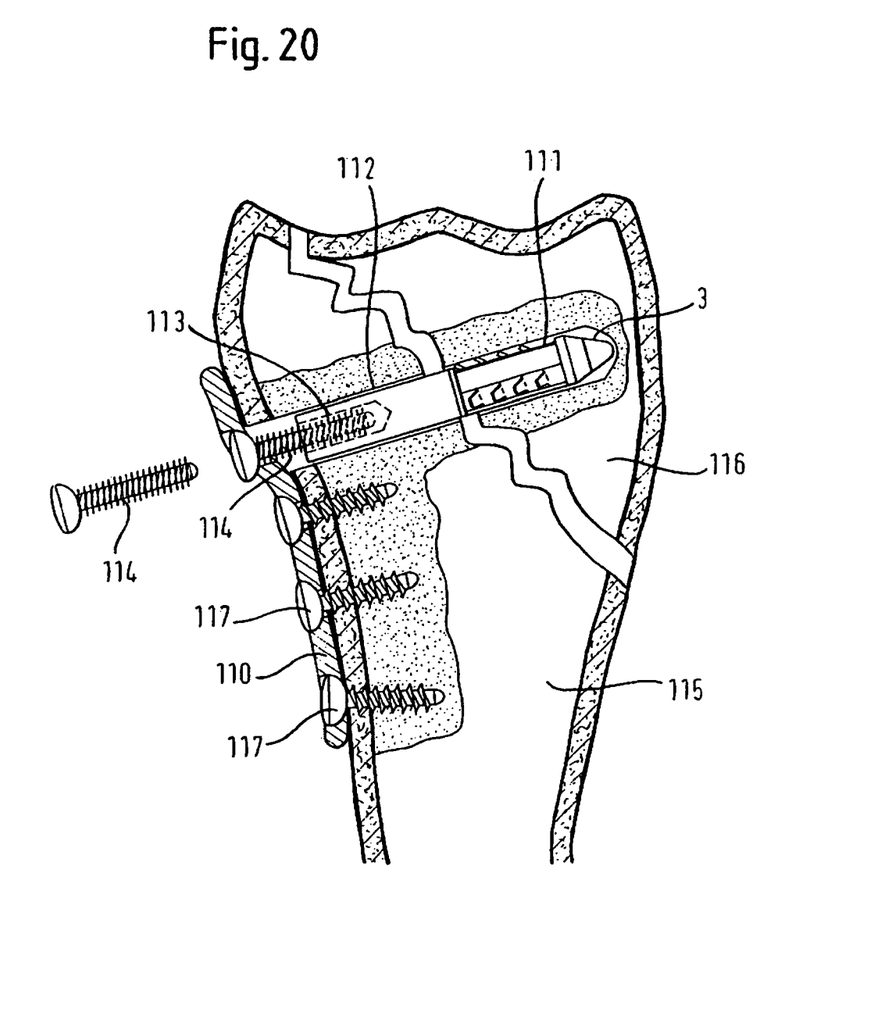
FIGS. 20-21 show an example of the application of the bone anchoring element in conjunction with a plate to fix a bone fracture.

FIG. 20 shows another application example, in which the bone anchoring element is used in conjunction with a plate, 110, to fix a bone fracture. Adjacent to tip 3, the bone anchoring element comprises a first shaft section, 111, which contains the barb elements, and adjacent to this first shaft section a second shaft section, 112, with a pocket hole bore, 113, with an internal thread, said pocket hole bore 113 extending from the end opposite to tip 3 towards the inside. A screw 114 is used to connect the bone anchoring element with plate 110. Screw, 114, can be screwed into the section of the bone anchoring element with an internal thread. In operation, the core hole bore is generated first in bone fragments 115, 116 to be fixed, followed by the insertion of the bone anchoring element. Here, the length of the core hole bore is such that section 111 with the barb elements and tip 3 of the anchoring element can be positioned in the one bone fragment, 116, and shaft section 112 with the internal thread can be positioned in the other bone fragment, 115. When screw 114 is screwed into bore hole 113 with the internal thread, the barb function of section 111, which is positioned in the one bone fragment, 116, causes the two bone fragments, 115, 116, to be pulled towards each other. Other screws, 117, may be provided for fixation of the plate.

Figure 21:
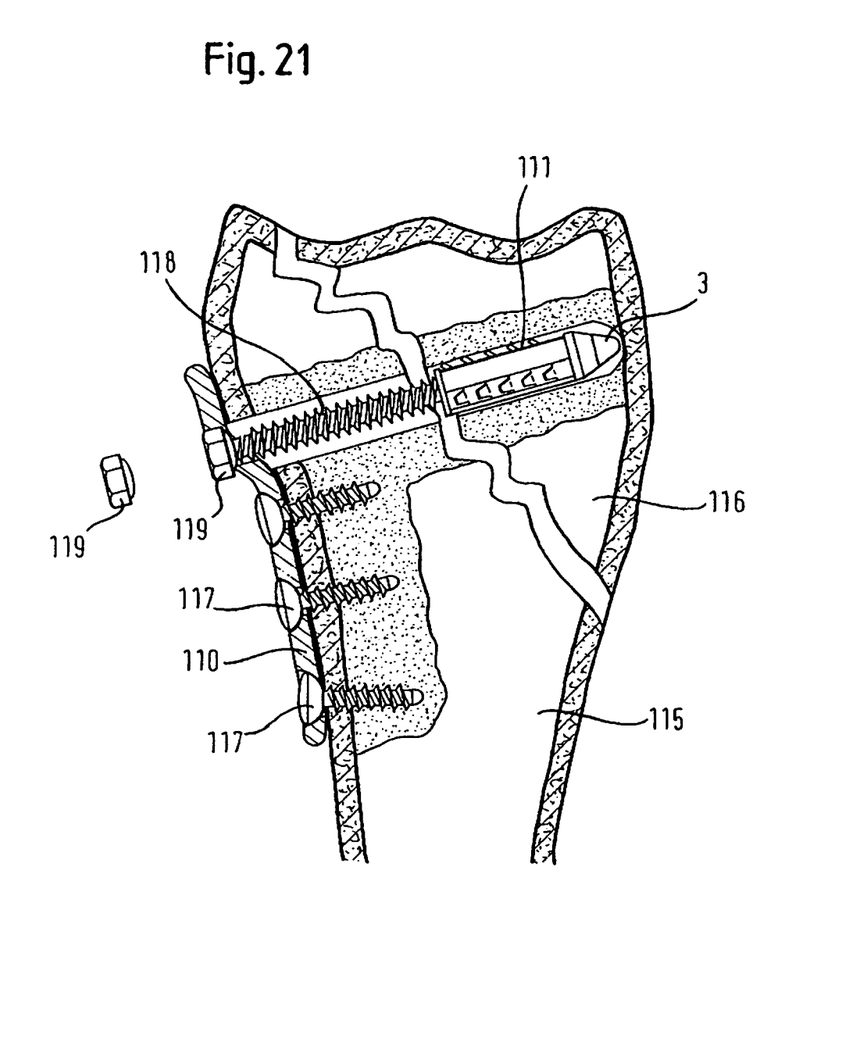

Another application example of the instant can be found in FIG. 21. The example shown in FIG. 21 differs from the application example of the bone anchoring element shown in FIG. 20 in that, in place of shaft section 112 with bore hole 113 having an internal thread, a shaft section, 118, with an external thread is provided adjacent to section 111 with the barb elements, onto which a external thread a nut, 119, can be screwed. The operation is identical to the application example shown in FIG. 20 with the exception that nut 119 is screwed on screw 114 instead of being screwed in.

Figure 22:
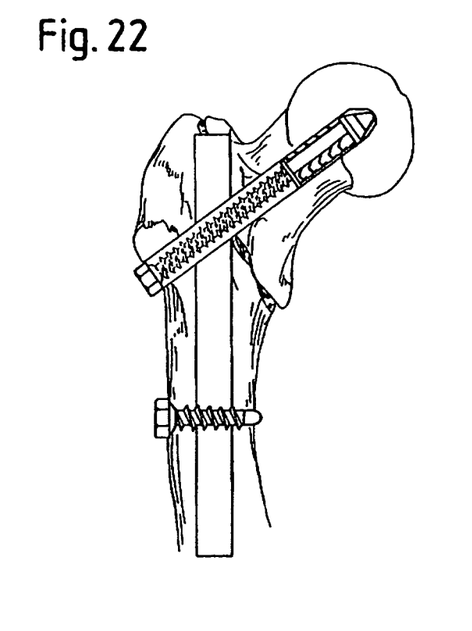
FIG. 22 shows an example of the application of the bone anchoring element in the hip.
Figure 23:
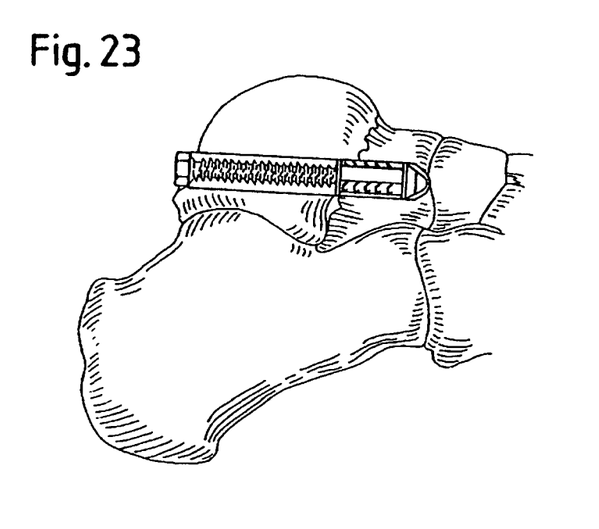
FIG. 23 shows an example of the application of the bone anchoring element in the ankle.

FIG. 22 shows another application example of the bone anchoring element of FIG. 21 as used in a hip joint to fix a hip fracture in conjunction with a supporting plate. One side of the plate is attached to the bone by a screw described in the second embodiment of this invention or with a conventional bone screw. The other side of the plate is attached by a screw described in FIG. 21. Similarly, FIG. 23 shows the bone anchoring element of FIG. 21 being used in an ankle to fix an ankle injury.

The embodiments described above and shown herein are illustrative and not restrictive. The scope of the invention is indicated by the claims, including all equivalents, rather than by the foregoing description and attached drawings. The invention may be embodied in other specific forms without departing from the spirit and scope of the invention. Accordingly, these and any other changes which come within the scope of the claims are intended to be embraced therein.

We claim:

1. A method of manufacturing a bone anchoring element with a first end, a second end, a longitudinal axis extending between the first and second ends, a tip at the first end configured for insertion into a bone, and a head at the second end configured for attachment to a connection element, the method comprising:

forming the bone anchoring element with the tip at the first end, the head at the second end, and a shaft extending between the tip and the head;

forming a thread on at least part of the shaft; and forming a plurality of rounded concave grooves in the thread after the thread is formed, wherein the grooves extend axially and separate the thread into a plurality of discrete spaced-apart barb elements positioned around the longitudinal axis, wherein each of the barb elements formed extends from a base to a free end positioned farther away from the longitudinal axis than the base, and wherein for at least a portion of the shaft that is positioned closer to the second end than to the first end, a width of each of the grooves in a circumferential direction is at least as wide as a width of the free end of each of the barb elements in the circumferential direction.

2. The method of claim 1, further comprising forming an undercut in the thread on a side of the thread facing the head prior to forming the plurality of grooves to increase elastic deformability of the thread at least partially in an axial direction.

3. The method of claim 2, wherein after forming the undercut in the thread, at least two axially adjacent portions of the thread are spaced apart from one another in the axial direction by a cylindrical surface.

4. The method of claim 1, wherein the head is formed as a spherical shaped segment configured to be attached to a connection element.

5. The method of claim 1, wherein forming the plurality of grooves comprises milling the bone anchoring element.

6. The method of claim 1, wherein each of the grooves extends parallel to the longitudinal axis.

7. The method of claim 1, wherein a pair of side walls corresponding respectively to two circumferentially adjacent barb elements is formed by a same first groove from among the grooves when the first groove is formed in the thread.

8. The method of claim 1, wherein the bone anchoring element comprises a shape memory alloy.

9. A bone anchoring element having a first end, a second end, and a longitudinal axis extending between the first and second ends, the bone anchoring element comprising:

a tip at the first end configured for insertion into a bone;

a head at the second end configured for attachment to a connection element; and a shaft extending between the tip and the head, the shaft comprising a plurality of discrete spaced-apart barb elements each having a base, a free end, and two circumferentially spaced apart side walls connecting the base with the free end, wherein a cylindrical surface extends in an axial direction between at least two of the barb elements that are adjacent to one another in a direction parallel to the longitudinal axis, and wherein the shaft defines a plurality of axially extending grooves that separate circumferentially adjacent ones of the barb elements;

wherein for a cross-section taken in a plane transverse to the longitudinal axis, at least a first groove from among the grooves has a rounded concave cross-sectional profile with an axis of symmetry that extends radially away from the longitudinal axis, and wherein one of the side walls of a first one of the barb elements and one of the side walls of a circumferentially adjacent second one of the barb elements each defines part of the cross-sectional profile of the first groove; and wherein the entire region of the bone anchoring element that extends between the tip and the head is a monolithic body having a solid core.

10. The bone anchoring element of claim 9, wherein each of the grooves extends parallel to the longitudinal axis.

11. The bone anchoring element of claim 9, wherein the barb elements are elastically deformable at least partially in the axial direction.

12. The bone anchoring element of claim 9, wherein the base of each barb element is at least as wide as the free end of the barb element in a circumferential direction.

13. The bone anchoring element of claim 9, wherein the bone anchoring element comprises a shape memory alloy.

14. A bone anchoring element having a first end, a second end, and a longitudinal axis extending between the first and second ends, the bone anchoring element comprising:
   a tip at the first end configured for insertion into a bone;
   a head at the second end configured for attachment to a connection element; and
   a shaft extending between the tip and the head, the shaft comprising a plurality of discrete spaced-apart barb elements that are elastically deformable at least partially in an axial direction, wherein each of the barb elements is monolithically formed with other parts of the shaft and has a base, a free end positioned farther away from the longitudinal axis than the base, and two circumferentially spaced apart side walls connecting the base with the free end;
   wherein the shaft defines a plurality of axially extending grooves that separate circumferentially adjacent barb elements, with a width of each of the grooves in the circumferential direction being at least as wide as a width of the free end of each of the barb elements in the circumferential direction; and
   wherein for a cross-section taken in a plane transverse to the longitudinal axis, a cross-sectional profile of a first groove from among the grooves is rounded and concave and has an axis of symmetry that extends radially away from the longitudinal axis, while one of the side walls of a first one of the barb elements and one of the side walls of a circumferentially adjacent second one of the barb elements each defines part of the cross-sectional profile of the first groove.

15. The bone anchoring element of claim 14, wherein each of the grooves extends parallel to the longitudinal axis.

16. The bone anchoring element of claim 14, wherein at least two of the barb elements are spaced apart from one another in the axial direction by a cylindrical surface.

17. The bone anchoring element of claim 14, wherein the entire region of the bone anchoring element that extends between the tip and the head is a monolithic body having a solid core.

18. The bone anchoring element of claim 14, wherein for the cross-section taken in the plane transverse to the longitudinal axis, the free end, the base, and the side walls of each barb element through which the plane extends form a cross-sectional trapezoidal shape.

19. The bone anchoring element of claim 14, wherein the bone anchoring element comprises a shape memory alloy.

20. The bone anchoring element of claim 14, wherein a radius of curvature of each of the grooves is greater than a radial distance between the longitudinal axis and the free end of each of the barb elements.

21. A bone anchoring element having a first end, a second end, and a longitudinal axis extending between the first and second ends, the bone anchoring element comprising:
   a tip at the first end configured for insertion into a bone;
   a head at the second end configured for attachment to a connection element; and
   a shaft extending between the tip and the head, the shaft comprising a plurality of discrete spaced-apart barb elements that are elastically deformable at least partially in an axial direction, wherein each of the barb elements is monolithically formed with other parts of the shaft and has a base, a free end positioned farther away from the longitudinal axis than the base, and two circumferentially spaced apart side walls connecting the base with the free end, wherein for a cross-section taken in a plane transverse to the longitudinal axis, the free end, the base, and the side walls of each barb element through which the plane extends form a cross-sectional trapezoidal shape;
   wherein the shaft defines a plurality of axially extending grooves that separate circumferentially adjacent barb elements, such that one of the side walls of a first one of the barb elements and one of the side walls of a circumferentially adjacent second one of the barb elements each defines part of a cross-sectional profile of a same one of the grooves, and wherein a width of each of the grooves in the circumferential direction is at least as wide as a width of the free end of each of the barb elements in the circumferential direction.

* * * * *